US009226987B2

(12) United States Patent
Gordon et al.

(10) Patent No.: US 9,226,987 B2
(45) Date of Patent: Jan. 5, 2016

(54) VOLATILE MATERIAL DISPENSER ALLOWING AIRFLOW AROUND A REFILL

(71) Applicant: S.C. Johnson & Son, Inc., Racine, WI (US)

(72) Inventors: William F. Gordon, Chicago, IL (US); Alex Mecker, Milwaukee, WI (US); Jason R. Gebhardt, Buffalo Grove, IL (US); Charlie Nghiem, San Francisco, CA (US); Jonathan Rathbone, Chicago, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 399 days.

(21) Appl. No.: 13/712,287

(22) Filed: Dec. 12, 2012

(65) Prior Publication Data

US 2014/0158790 A1    Jun. 12, 2014

(51) Int. Cl.
*A01M 1/20* (2006.01)
*A61L 9/12* (2006.01)

(52) U.S. Cl.
CPC .............. *A61L 9/127* (2013.01); *A01M 1/2044* (2013.01); *A61L 2209/133* (2013.01)

(58) Field of Classification Search
CPC ......... A61L 9/12; A61L 9/127; A01M 1/2044
USPC ..................... 239/34, 44, 47, 49, 50, 51.5, 55
See application file for complete search history.

(56) References Cited

U.S. PATENT DOCUMENTS

| D86,118 | S | 2/1932 | Fuerst |
| D87,167 | S | 6/1932 | Noble |
| D94,416 | S | 1/1935 | Green |
| D138,198 | S | 7/1944 | Jackson |
| 2,796,290 | A | 6/1957 | Downs |
| 3,923,178 | A | 12/1975 | Welker, III |
| D355,601 | S | 2/1995 | Buettner et al. |
| D369,558 | S | 5/1996 | Heinz |
| D418,061 | S | 12/1999 | Starker |
| D431,779 | S | 10/2000 | Nosella |
| D480,315 | S | 10/2003 | Sadeghi et al. |
| 7,032,831 | B2 * | 4/2006 | Duston et al. ............ 239/44 |
| D564,357 | S | 3/2008 | Kapoor et al. |
| D612,740 | S | 3/2010 | Leone |
| 7,837,930 | B2 | 11/2010 | Grodsky |
| D644,515 | S | 9/2011 | Tieleman et al. |
| D651,518 | S | 1/2012 | Padain et al. |

(Continued)

FOREIGN PATENT DOCUMENTS

| GB | 2462274 A | 2/2010 |
| WO | WO2012/009018 A1 | 1/2012 |
| WO | WO2012/175982 A1 | 12/2012 |

OTHER PUBLICATIONS

PCT/US2013/074541 International Search Report and Written Opinion dated Jun. 17, 2014.

*Primary Examiner* — Arthur O Hall
*Assistant Examiner* — Viet Le (57) ABSTRACT

A refill adapted for use with a volatile material dispenser comprises a body adapted to hold a volatile material and a wick disposed within the body and extending out of the refill. The wick is adapted to transport the volatile material from the body out of the refill. One or more features of the refill allow the refill to be easily inserted into a volatile material dispenser and/or allow air to flow around the refill.

17 Claims, 12 Drawing Sheets

(56) References Cited

U.S. PATENT DOCUMENTS

| | | |
|---|---|---|
| D658,915 S | 5/2012 | Fernandes et al. |
| 2010/0215549 A1 | 8/2010 | Corda |
| 2011/0139890 A1* | 6/2011 | Soldan et al. ................... 239/44 |
| 2011/0139892 A1* | 6/2011 | Gasper et al. ................... 239/44 |
| 2012/0012552 A1 | 1/2012 | Kubicek et al. |

* cited by examiner

VOLATILE MATERIAL DISPENSER ALLOWING AIRFLOW AROUND A REFILL

BACKGROUND

1. Field of the Invention

The present invention relates generally to refills and, more particularly, to refills for holding volatile materials.

2. Description of the Background

Devices that release vapors into the air are well-known in the art. Generally, the purpose of such devices is to deodorize, disinfect, or add positive fragrance to the ambient air, or to distribute insect repellants or insecticides into the air to kill or repel unwanted pests, such as mosquitoes and gnats.

Various types of devices have been employed to dispense vapors into the air. For example, passive dispensing devices are known, wherein a volatile material in a gel, liquid, or solid form is provided within a container. The volatile material is diffused into the surrounding atmosphere, and the diffusion may be assisted by the natural airflow within the surroundings. A vent may be included in such passive dispensing devices to increase and decrease the amount of volatile material emitted from the passive dispensing devices. Aerosol containers have also been employed to eject droplets of volatile material from a pressurized container into a surrounding atmosphere upon activation of a trigger.

Other devices have utilized mechanical or electrical devices to dispense volatile materials into the atmosphere. In one such device, a container having a porous wick disposed therein in contact with a liquid volatile material and extending out a neck of the container is disposed within a diffusion device. The volatile material travels through the porous wick to an exposed end thereof. The diffusion device may include a heater and/or a fan disposed adjacent the exposed end of the wick to assist in the volatilization and/or dispersion of the liquid volatile material in the wick. Optionally, the container with porous wick and volatile material may be positioned to emit volatile material therefrom without being disposed within a diffusion device.

Containers or refills having wicks in contact with a volatile material generally include a reservoir portion for holding the volatile material and a neck portion that forms an opening in communication with the reservoir portion. A plug assembly is disposed within the neck portion, wherein the plug assembly includes a hole through a central portion thereof for accommodating the wick. If used in combination with a volatile material dispenser, containers and plug assemblies of different refills are generally configured to fit within a particular volatile material dispenser. Such containers and/or plug assemblies may also be configured to retain the refill within the volatile material dispenser. For example, one commercial refill includes a container having a body with front and rear walls having projections extending outwardly therefrom. The projections interact with features in the volatile material dispenser to retain the refill within the volatile material dispenser.

SUMMARY

In an illustrative embodiment, a refill adapted for use with a volatile material dispenser comprises a body adapted to hold a volatile material and a wick disposed within the body and extending out of the refill. The wick is adapted to transport the volatile material from the body out of the refill. A longitudinal axis of the body extends through a center of the body and the body is rotationally symmetrical about the longitudinal axis.

In a further illustrative embodiment, a refill adapted for use with a volatile material dispenser comprises a body adapted to hold a volatile material. A wick is disposed within the body and extends out of the refill, wherein the wick is adapted to transport the volatile material from the body out of the refill. The body includes a plurality of walls each having first and second vertices shared with adjacent walls, an upper edge, and a lower edge adjacent a bottom wall of the body, wherein each of the walls is curved inwardly between the side edges to form flutes.

In another illustrative embodiment, a volatile material dispenser comprises a housing including a first feature for retaining a refill and a refill retained within the housing. The refill includes a body adapted to hold a volatile material, wherein the body includes a second feature adapted to interact with the first feature within a volatile material dispenser to retain the refill within the volatile material dispenser. The refill further includes a neck extending outwardly from the body and a wick disposed within the body and extending out of the refill through the neck. A longitudinal axis of the body extends through a center of the body and the body is rotationally symmetrical about the longitudinal axis so the body may be rotated and inserted into the dispenser at any point about 360 degrees of the longitudinal axis.

BRIEF DESCRIPTION OF THE DRAWINGS

Other aspects and advantages of the present invention will become apparent upon consideration of the following detailed description, wherein similar structures have like or similar reference numerals.

DETAILED DESCRIPTION

The present invention is directed to refills for holding volatile materials. While the refills of the present invention may be embodied in many different forms, several specific embodiments are discussed herein with the understanding that the present invention is to be considered only as an exemplification of the principles of the invention, and it is not intended to limit the invention to the embodiments illustrated.

Figure 1:
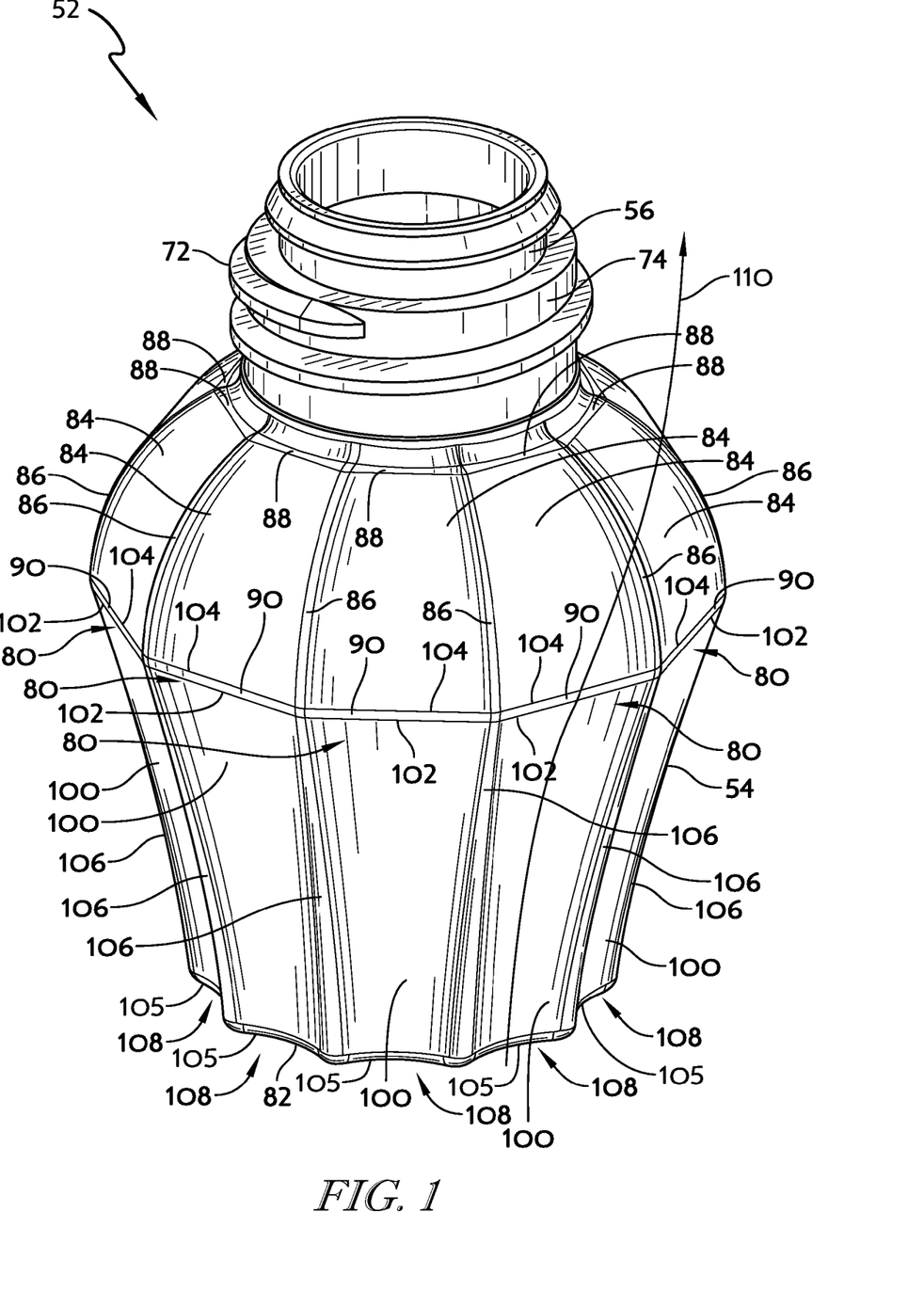
FIG. 1 is a top isometric view of a first embodiment of a refill with a plug assembly and wick removed therefrom.
Figure 2:
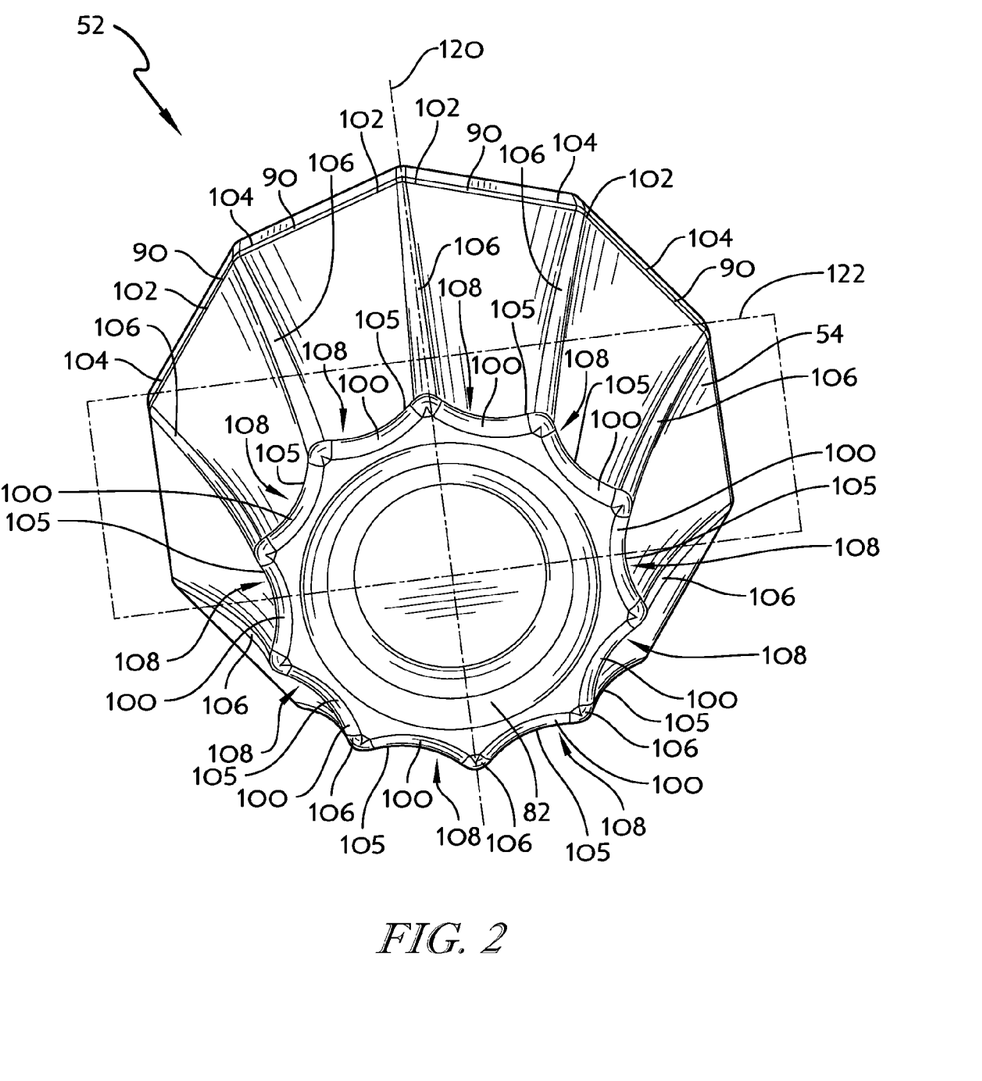
FIG. 2 is a bottom isometric view of the refill of FIG. 1.

Referring to the drawings, FIGS. 1-5 depict a first embodiment of a refill 50 for holding a volatile material. The refill 50 generally includes a container 52 for holding the volatile material therein. The refill 50 may be retained within a housing of a volatile material dispenser or, alternatively, may be used independently, for example, on a surface of a consumer's home. As seen in FIG. 2, the container 52 generally includes a body 54 for holding the volatile material and a generally cylindrical neck 56 extending away from the body 54 and in communication with an interior of the body 54.

Figure 3:
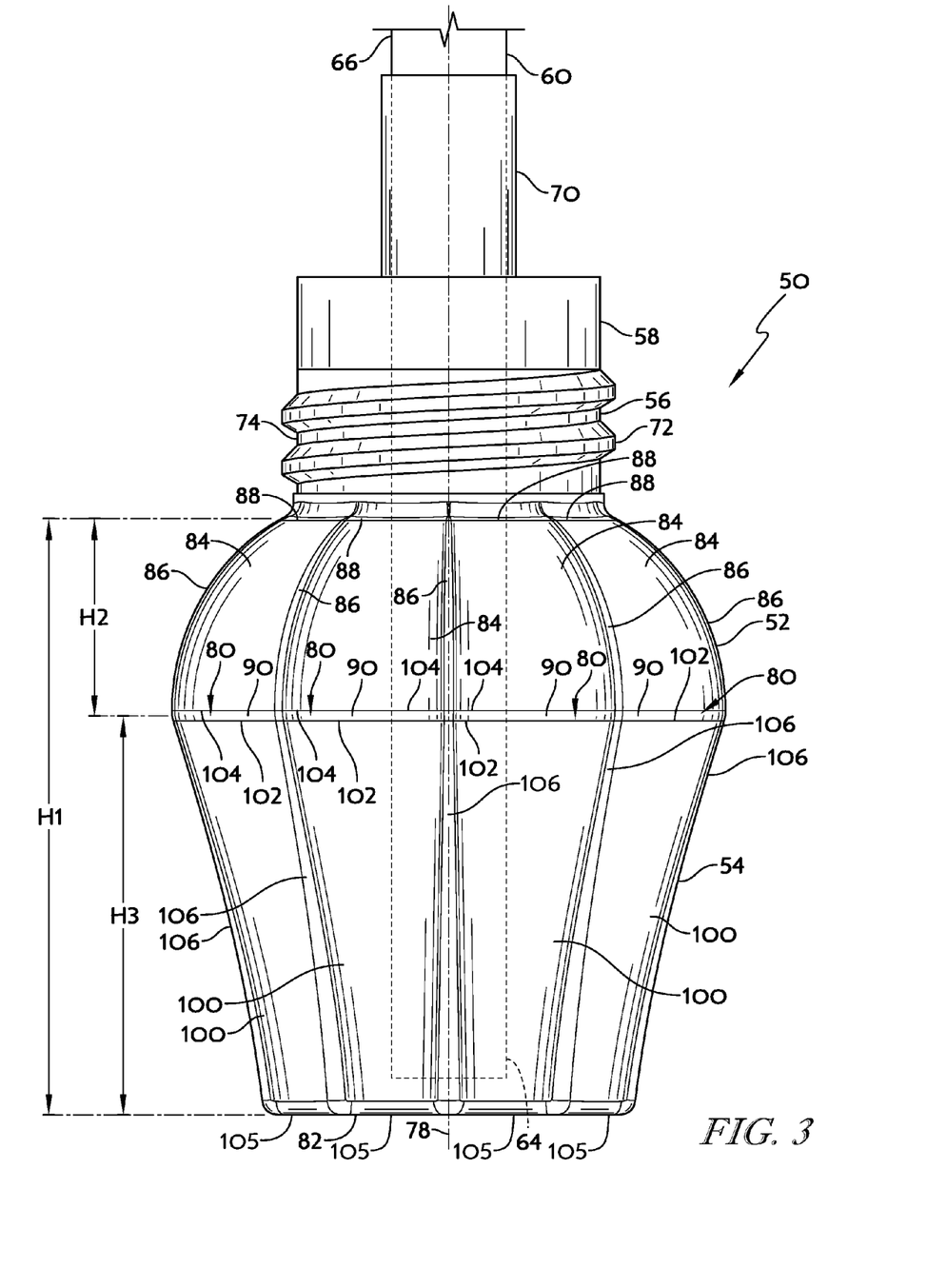
FIG. 3 is a side elevational view of the refill of FIG. 1 and depicting the plug assembly and wick within the refill.

A plug assembly 58 is secured within the neck 56 of the container 52 for positioning a porous wick 60 within the container 52. In particular, the plug assembly 58 positions the porous wick 60 with a first end 64 of the wick 60 in contact with the volatile material within the container 52 and a second end 66 of the wick 60 extending out of the container 52 through the neck 56. The porous wick 60 serves to transport the volatile material in the body 54 of the container 52 from the first end 64 of the wick 60 to the second end 66 of the wick 60 through capillary action, such that volatile material may be emitted from the second end 66 of the wick 60 into the ambient air. A sheath 70 may be formed integrally with the plug assembly 58 and may extend away from the container 52. If present, the sheath 70 surrounds and protects a portion of the wick 60, for example, from heat emitted by a heater disposed within a volatile material dispenser.

A plurality of threads 72 may be disposed on an outer periphery 74 of the neck 56. The threads 72 may aid in attaching and/or retaining a cap (not shown) on the neck 56 to enclose the second end 66 of the wick 60 during, for example, shipment or storage. Additionally or optionally, the threads 72 may aid in securing the refill 50 to a volatile material dispenser. Still optionally, the refill 150 may include any additional or alternative feature(s) for attaching the refill 150 to a volatile material dispenser.

Figure 4:
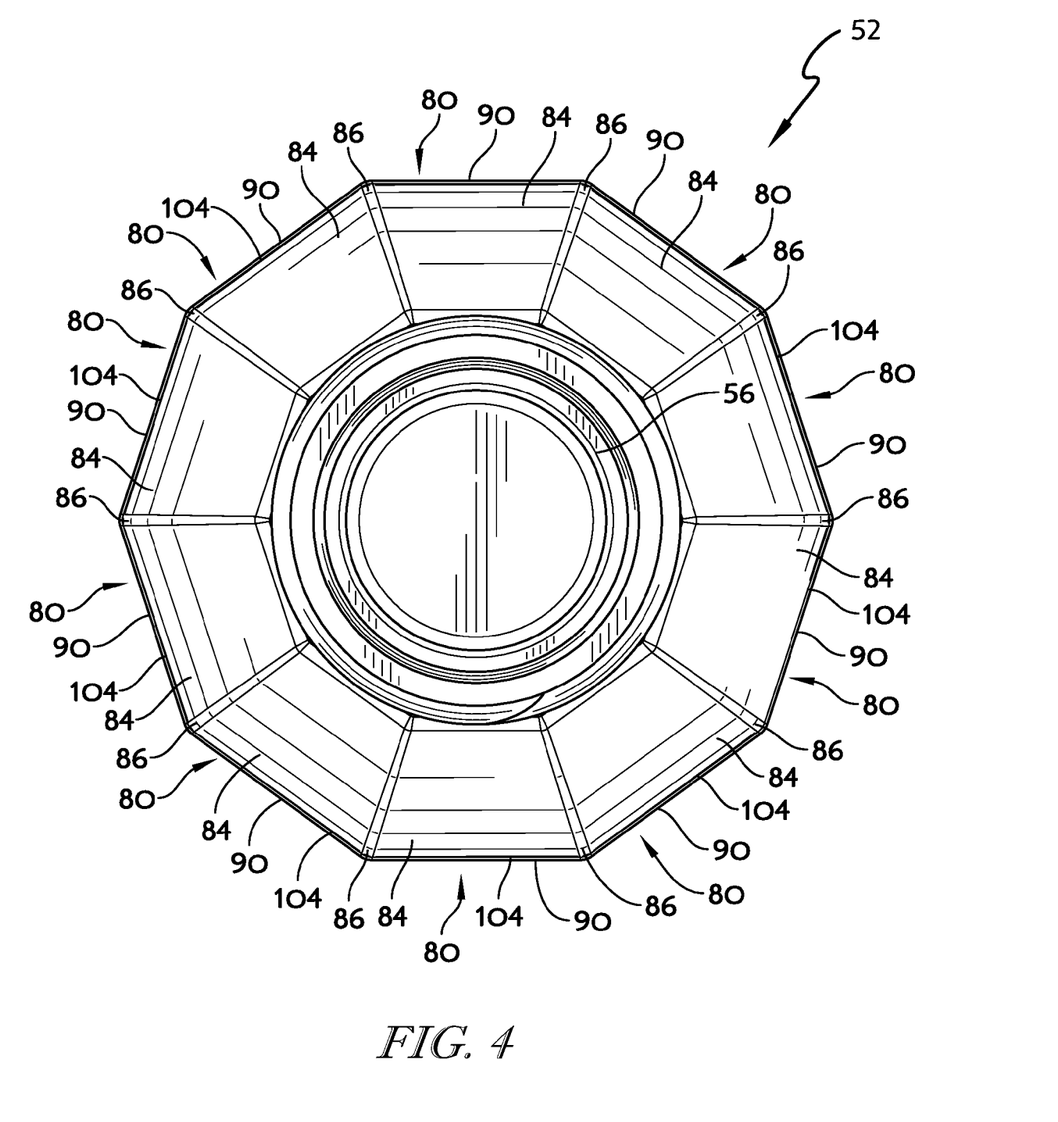
FIG. 4 is a top elevational view of the refill of FIG. 1.

As seen in FIGS. 1-5, the body 54 has a height H1 that extends along a longitudinal axis 78 of the container 52, wherein the longitudinal axis 78 extends through a center of the body 54 (and optionally the wick 60). The body 54 includes a plurality of walls 80 extending between the neck 56 and a bottom wall 82 of the container 52. Each wall 80 includes a first wall portion 84 that is connected to and curves outwardly and downwardly from the neck 56 of the container 52. As best seen in FIG. 4, each first wall portion 84 shares a side edge or vertex 86 with an adjacent first wall portion 84. Each first wall portion 84 includes a top edge 88 that is integrally formed with the neck 56 and a bottom edge 90. Each first wall portion 84 extends between adjacent vertices 86. In an illustrative embodiment, the first wall portions 84 have a height H2 that is about 0.56 inch (14.2 mm) or about 35% of the height H1 of the body 54. In other illustrative embodiments, the height H2 is between about 10% and about 50% of the height H1. In still other illustrative embodiments, the height H2 is between about 25% and about 40% of the height H1.

Figure 11:
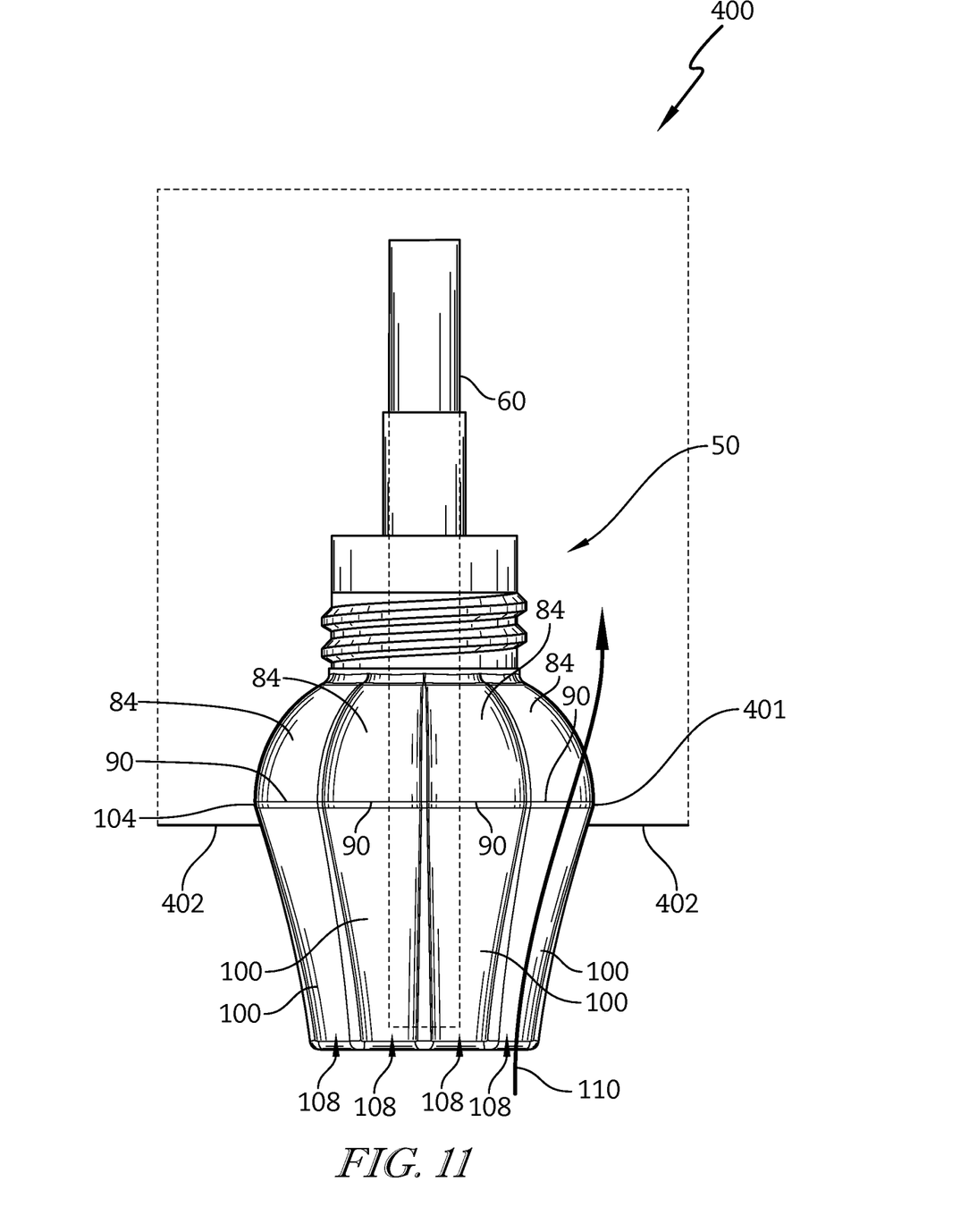
FIG. 11 is a cross-sectional view of a volatile material dispenser with the refill of FIGS. 1-5 retained therein.

Each wall 80 of the body 54 further includes a second plurality of wall portions 100 extending between a top edge 102 that is integral and coincident with and forms a transition point 104 with the bottom edge 90 of a respective first wall portion 84 and a bottom edge 105 that is integral with the bottom wall 82 of the container 52. As best seen in FIG. 3, each of the second wall portions 100 tapers inwardly from the transition points 104 to the bottom edge 105 of each second wall portion 100, thereby creating a ledge 401 at the transition points 104 that may be utilized for retaining the refill 50 within a volatile material dispenser, for example, within the volatile material dispenser 400 of FIG. 11. A retention feature 402 may interact with the ledge to retain the refill 50. In an illustrative embodiment, the second wall portions 100 have a height H3 that is about 1.04 inch (26.4 mm) or about 65% of the height H1 of the body 54. In other illustrative embodiments, the height H3 is between about 50% and about 90% of the height H1. In still other illustrative embodiments, the height H3 is between about 60% and about 75% of the height H1.

Figure 5:
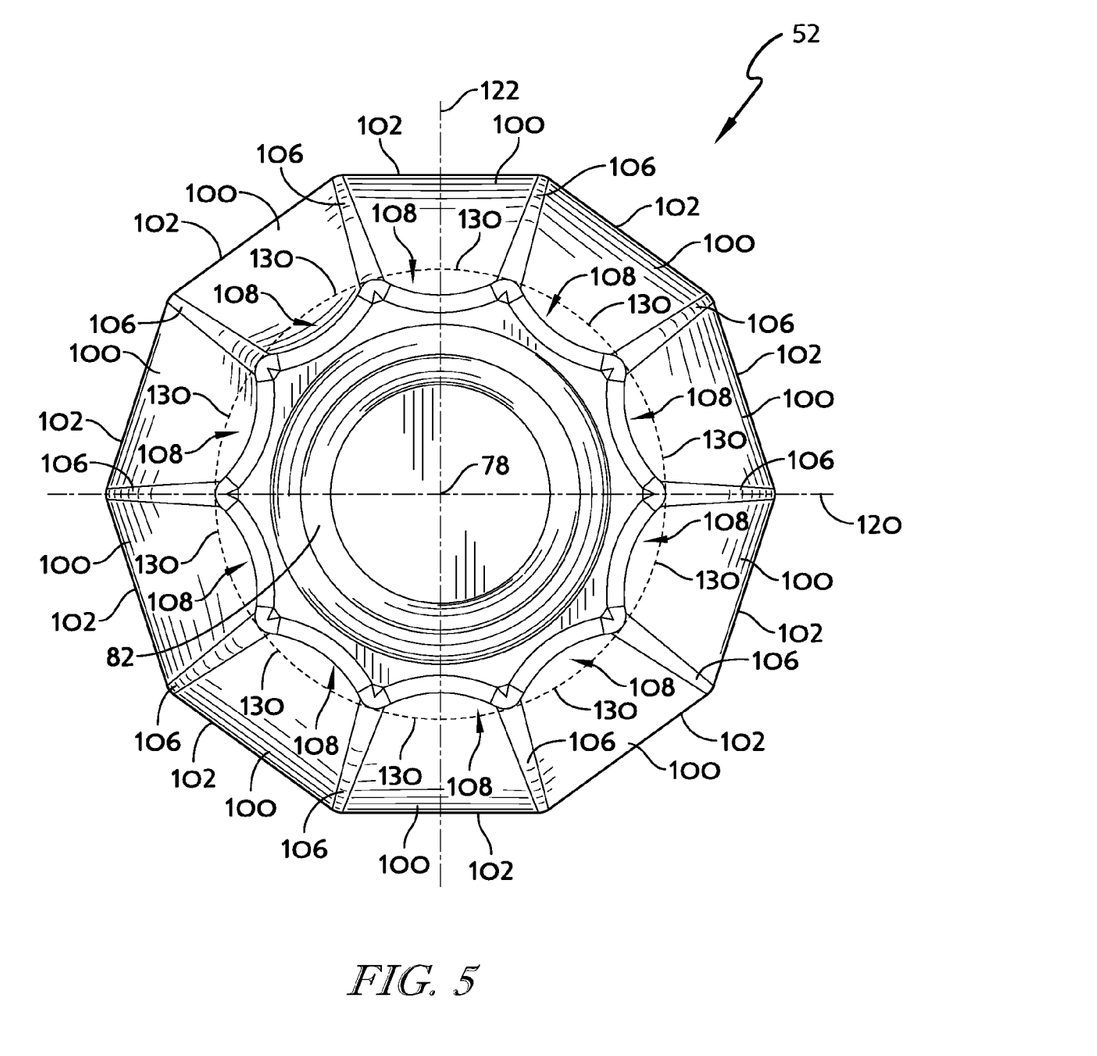
FIG. 5 is a bottom elevational view of the refill of FIG. 1.

Referring to FIGS. 2 and 5, each second wall portion 100 shares a side edge or vertex 106 with adjacent second wall portions 100, wherein each second wall portion 100 extends between adjacent vertices 106. The second wall portions 100 are concave such that they create flutes 108 between the vertices 106. As best seen in FIG. 5, the flutes 108 create gaps between the vertices 106, thereby creating airflow paths along the second wall portions 100. In illustrative embodiments, the flutes 108 may have a radius of curvature of between about 0.1 inch (2.54 mm) and about 0.4 inch (10.16 mm) at the bottom edge 105 of the second wall portion 100. In an illustrative embodiment, the radius of curvature for each flute 108 is the same. In another illustrative embodiment, the radius of curvature of each flute 108 may be different or any number of the flutes 108 may have different radii of curvature. When a typical refill is inserted into and retained within a volatile material dispenser, the refill is generally held in a manner in which airflow around the refill and into the dispenser is restricted. In contrast, when the refill 50 is inserted into the dispenser 400, the flutes 108 allow air to flow past the refill 50 to cool the dispenser 400, aid in volatile material emission, and/or provide any other suitable benefits. In particular, air may flow up the flutes 108, around the bottom edges 90 of the first wall portions 84 and through the dispenser 400, as shown by arrow 110 in FIGS. 1 and 11.

As best seen in FIGS. 2 and 5, the refill 50 is symmetrical. In particular, the refill 50 is symmetrical about a first plane 120 that bisects the refill 50, comprises the longitudinal axis 78, and extends through two opposing sets of vertices 86, 106. The plane 120 may be rotated to extend through any two opposing sets of vertices 86, 106 and the refill 50 will still be symmetrical about the plane 120. This symmetry will be referred to herein as rotational symmetry through 360 degrees about the longitudinal axis 78 (or about the plane 120). Still referring to FIGS. 2 and 5, the refill 50 is also symmetrical about a second plane 122 that is perpendicular to the first plane 120, bisects the refill 50, comprises the longitudinal axis 79, and bisects two opposing wall portions 84, 100. As with the plane 120, the plane 122 may be rotated to bisect any two opposing first and second wall portions 84, 100 and the refill 50 will still be symmetrical about the plane 122. This again depicts the rotational symmetry of the refill 50 about the longitudinal axis 78 (and the plane 122).

The refill 50 is depicted as having rotational symmetry of the order 20 or 20-fold rotational symmetry with respect to the first plane 120 and rotational symmetry of the order 20 or 20-fold rotational symmetry with respect to the second plane 122. In this manner, if either of the planes 120, 122 is rotated 18 degrees, the refill 50 remains symmetrical about the longitudinal axis 78 and with respect to the respective plane 120, 122. While the refill 50 is depicted and described as having rotational symmetry on the order of 20 about one or both of the planes 120, 122, in illustrative embodiments, the refill 50 may have rotational symmetry about one or both of the planes 120, 122 of between 4-fold and 36-fold. In such illustrative embodiments, the refill 50 would be symmetrical if either of the planes 120, 122 were rotated between about 10 degrees and about 90 degrees. In other illustrative embodiments, the refill 50 may have rotational symmetry about one or both of the planes 120, 122 of between 12-fold and 20-fold. In these illustrative embodiments, the refill 50 would be symmetrical if either of the planes 120, 122 were rotated between about 18 degrees and about 30 degrees.

The rotational symmetry of the refill 50 allows the refill 50 to be inserted and retained within a diffusion device in many different manners, thereby allowing for easy and proper installation of the refill 50. Specifically, many prior art refills may be inserted and retained within a diffusion device in a single orientation, or possibly two orientations (e.g., in a first orientation and a second orientation rotated 180 degrees about a longitudinal axis of the refill from the first orientation). The rotational symmetry of the refill 50 therefore allows the refill 50 to be easily inserted into and retained within a diffusion device in whatever rotational orientation a user positions the refill 50.

Referring again to FIG. 5, if arcs 130 are drawn to connect each of the vertices 106 with an adjacent vertex 106, a circle 132 is formed. Each arc 130 is depicted as forming a sector of about 36 degrees of the entire circle 132. In an illustrative embodiment, each arc 130 may form a sector of the circle 132 of between about 18 degrees and about 90 degrees. In another illustrative embodiment, each arc 130 may form a sector of the circle of between about 30 degrees and about 45 degrees. A profile of the refill 50 may be circular at the bottom edges 105 of the second wall portions 100 or in any plane formed perpendicular to the planes 102, 122 along the first or second wall portions 84, 100.

Figure 6:
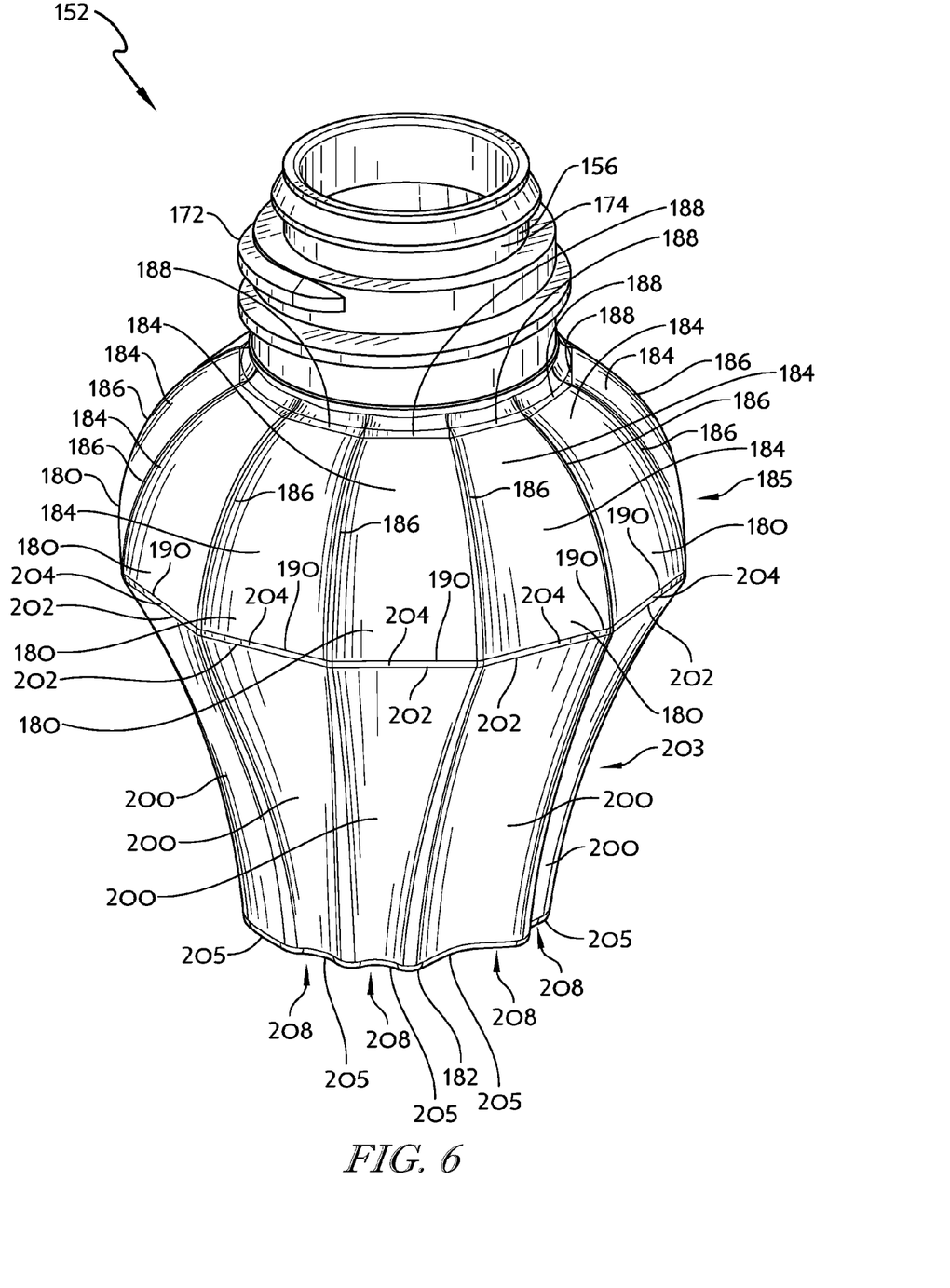
FIG. 6 is a top isometric view of a second embodiment of a refill with a plug assembly and wick removed therefrom.
Figure 7:
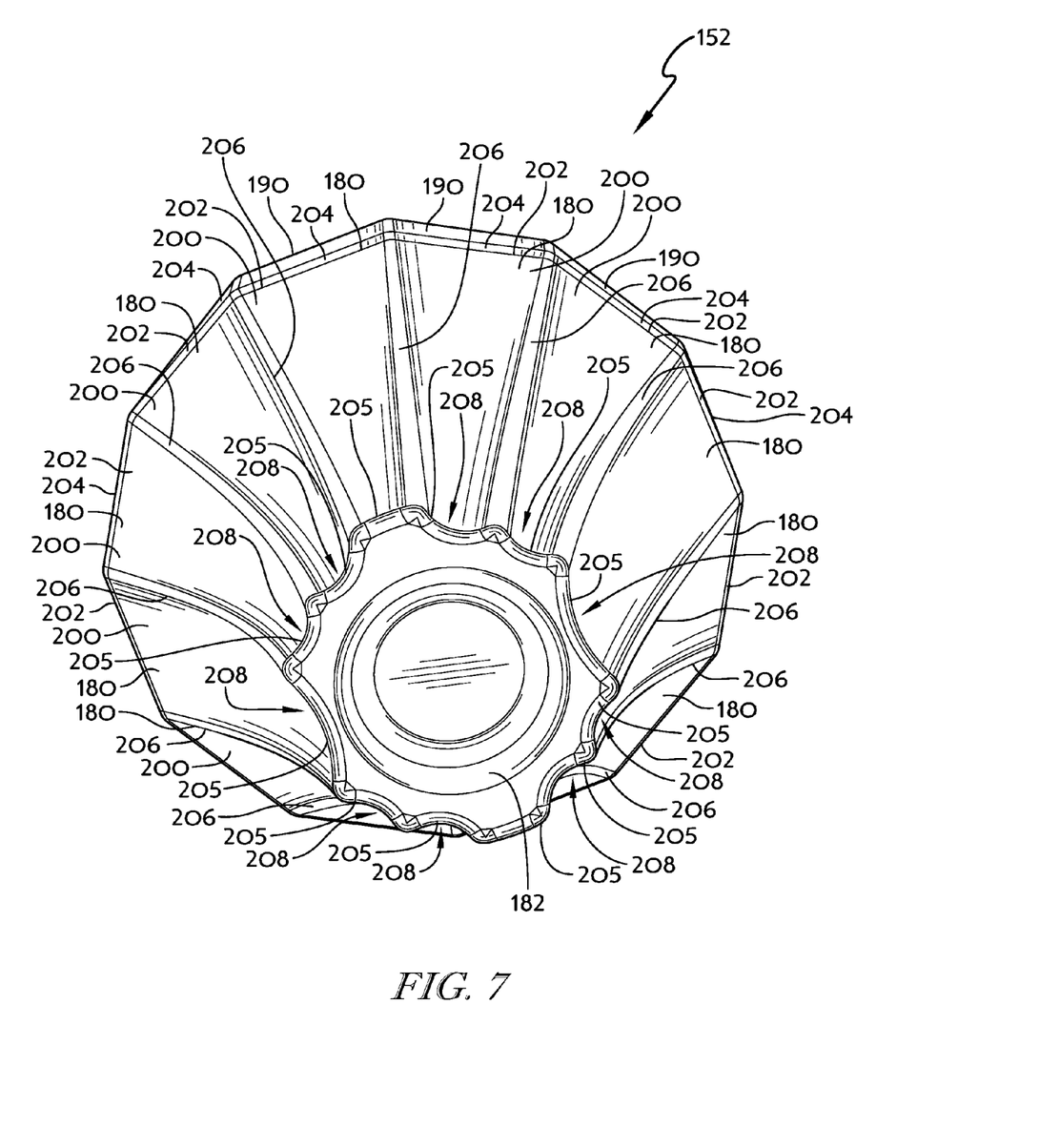
FIG. 7 is a bottom isometric view of the refill of FIG. 5.
Figure 8:
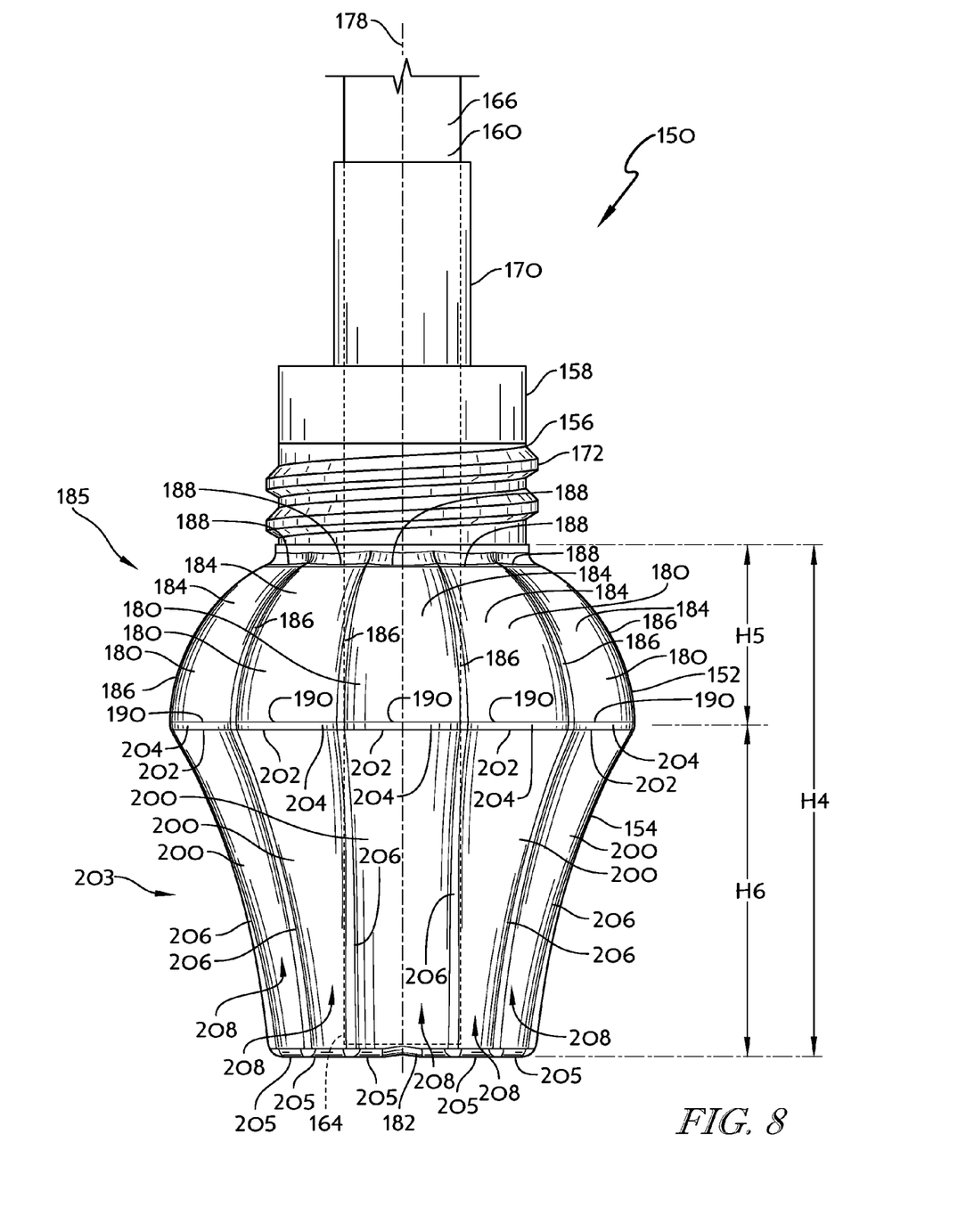
FIG. 8 is a side elevational view of the refill of FIG. 5 and depicting the plug assembly and wick within the refill.

A second embodiment of a refill 150 for holding a volatile material is depicted in FIGS. 6-10. The refill 150 generally includes a container 152 for holding the volatile material therein. The refill 150 may be retained within a housing of a volatile material dispenser or, alternatively, may be used independently, for example, on a surface of a consumer's home. As best seen in FIG. 8, the container 152 generally includes a body 154 for holding the volatile material and a generally cylindrical neck 156 extending away from the body 154 and in communication with an interior of the body 154.

A plug assembly 158 is secured within the neck 156 of the container 152 for positioning a porous wick 160 within the container 152. In particular, the plug assembly 158 positions the porous wick 160 with a first end 164 of the wick 160 in contact with the volatile material within the container 152 and a second end 166 of the wick 160 extending out of the container 152 through the neck 156. The porous wick 160 serves to transport the volatile material in the body 154 of the container 152 from the first end 164 of the wick 160 to the second end 166 of the wick 160 through capillary action, such that volatile material may be emitted from the second end 166 of the wick 160 into the ambient air. A sheath 170 may be formed integrally with the plug assembly 158 and may extend away from the container 152. If present, the sheath 170 surrounds and protects a portion of the wick 160.

A plurality of threads 172 may be disposed on an outer periphery 174 of the neck 156. The threads 172 may aid in attaching and/or retaining a cap (not shown) on the neck 156 to enclose the second end 166 of the wick 160 during, for example, shipment or storage. Additionally or optionally, the threads 172 may aid in securing the refill 150 to a volatile material dispenser. Still optionally, the refill 150 may include any additional or alternative feature(s) for attaching the refill 150 to a volatile material dispenser.

Figure 9:
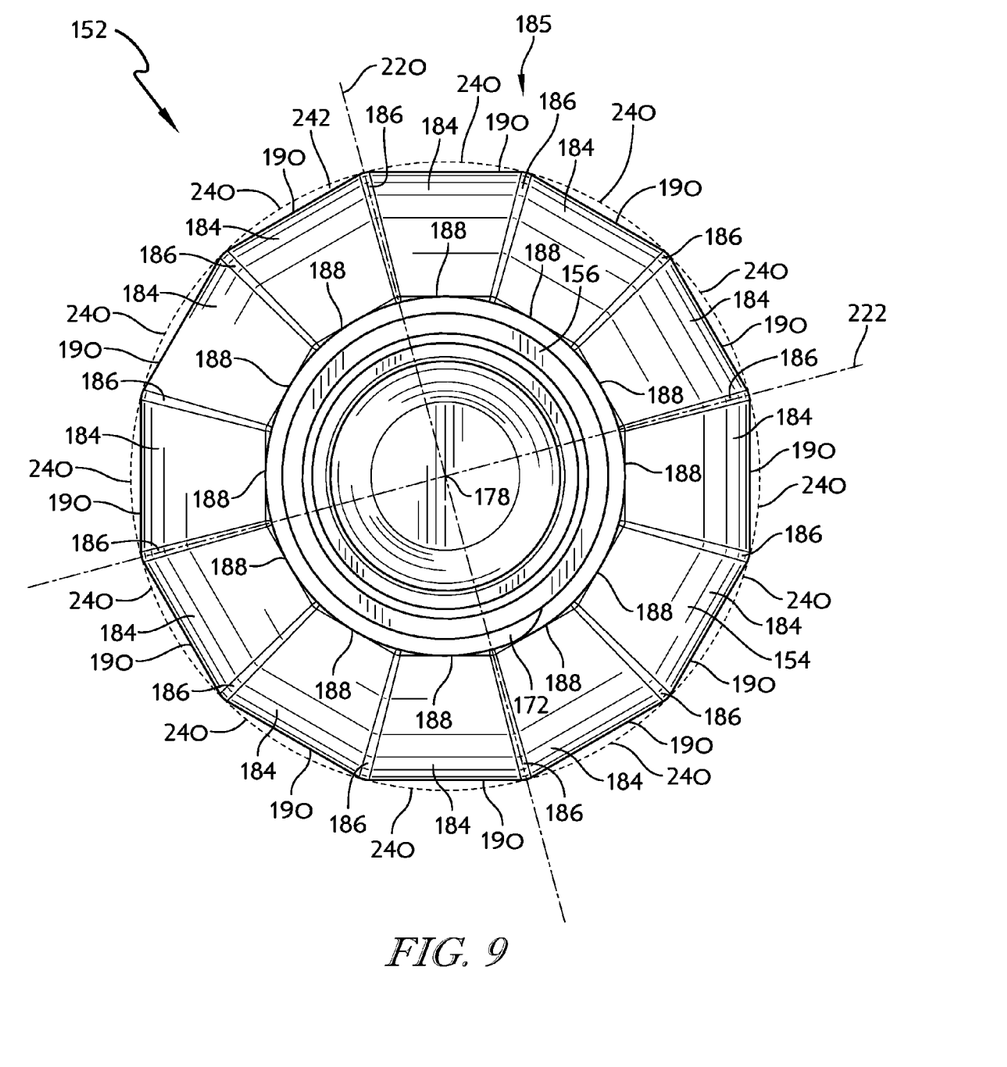
FIG. 9 is a top elevational view of the refill of FIG. 5.

As seen in FIGS. 6-10, the body 154 has a height H4 that extends along a longitudinal axis 178 of the container 152, wherein the longitudinal axis 178 extends through a center of the body 154 (and optionally the wick 160). The body 154 includes a plurality of walls 180 extending between the neck 156 and a bottom wall 182 of the container 152. Each wall 180 includes a first wall portion 184 that is connected to and curves outwardly and downwardly from the neck 156 of the container 152 to form a top portion 185 of the body 154. As best seen in FIGS. 6, 8, and 9, each first wall portion 184 shares a side edge or vertex 186 with adjacent first wall portions 184. Each first wall portion 184 includes a top edge 188 that is integrally formed with the neck 156 and a bottom edge 190 that is generally straight. Each first wall portion 184 extends between adjacent vertices 186. In an illustrative embodiment, the first wall portions 184 have a height H5 that is about 0.56 or about 38% of the height H4 of the body 154. In other illustrative embodiments, the height H5 is between about 10% and about 50% of the height H4. In still other illustrative embodiments, the height H5 is between about 25% and about 40% of the height H4.

Figure 12:
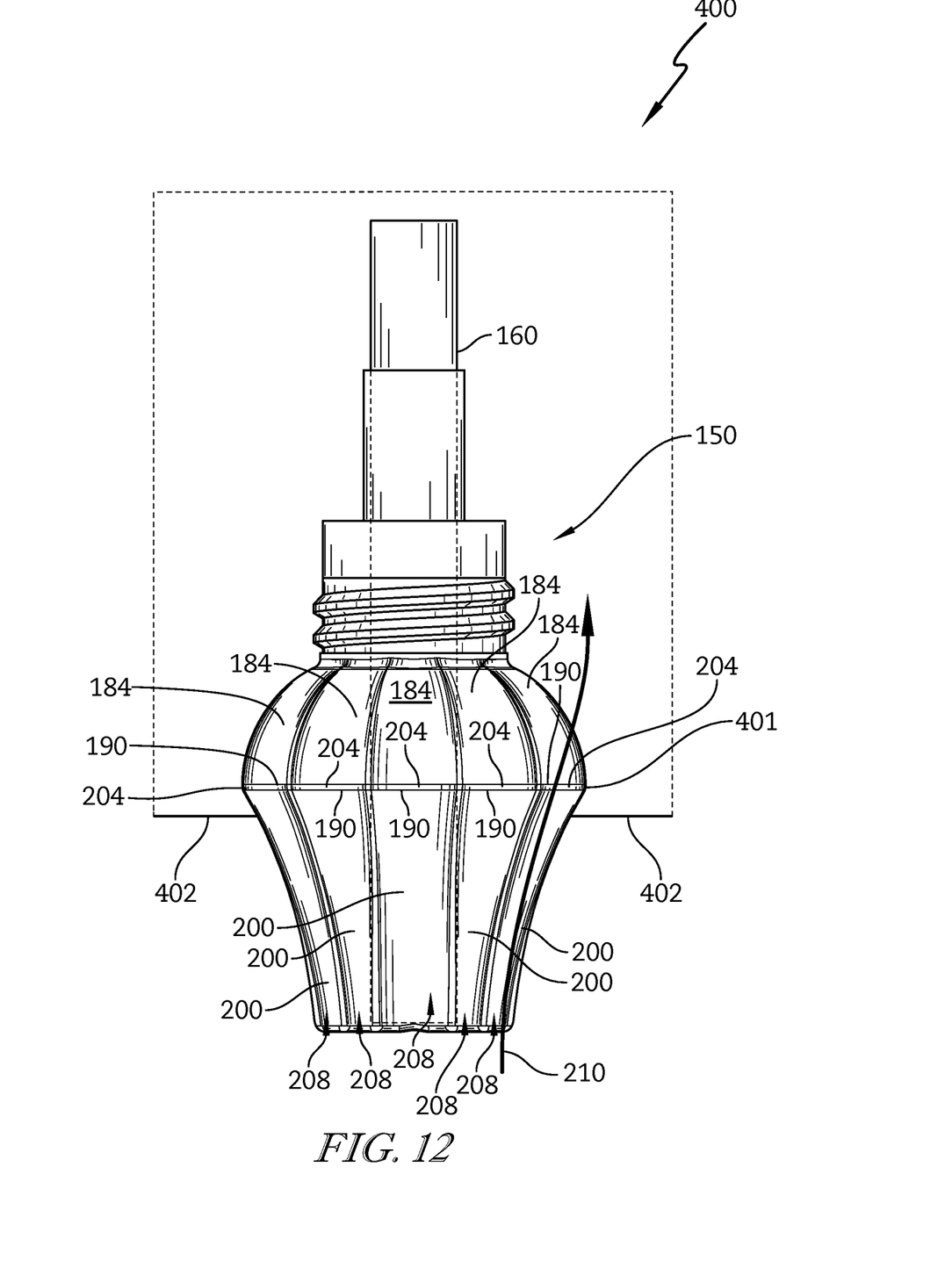
FIG. 12 is a cross-sectional view of the volatile material dispenser of FIG. 11 with the refill of FIGS. 6-10 retained therein.

Each wall 180 of the body 154 further includes a second plurality of wall portions 200 extending between a top edge 202 that is integral and coincident with and forms a transition point 204 with the bottom edge 190 of a respective first wall portion 184 and a bottom edge 205 that is integral with the bottom wall 182 of the container 152. The second wall portions 200 form a bottom portion 203 of the body 154. As best seen in FIG. 8, each of the second wall portions 100 curves inwardly from the transition points 204 to the bottom edge 205 of each second wall portion 100, thereby creating a ledge 401 at the transition points 204 that may be utilized for retaining the refill 150 within a volatile material dispenser, for example, within the volatile material dispenser 400 of FIG. 12. A retention feature 402 may interact with the ledge 401 to retain the refill 150. In an illustrative embodiment, the second wall portions 200 have a height H6 that is about 0.92 or about 62% of the height H1 of the body 54. In other illustrative embodiments, the height H6 is between about 50% and about 90% of the height H4. In still other illustrative embodiments, the height H6 is between about 60% and about 75% of the height H4.

Figure 10:
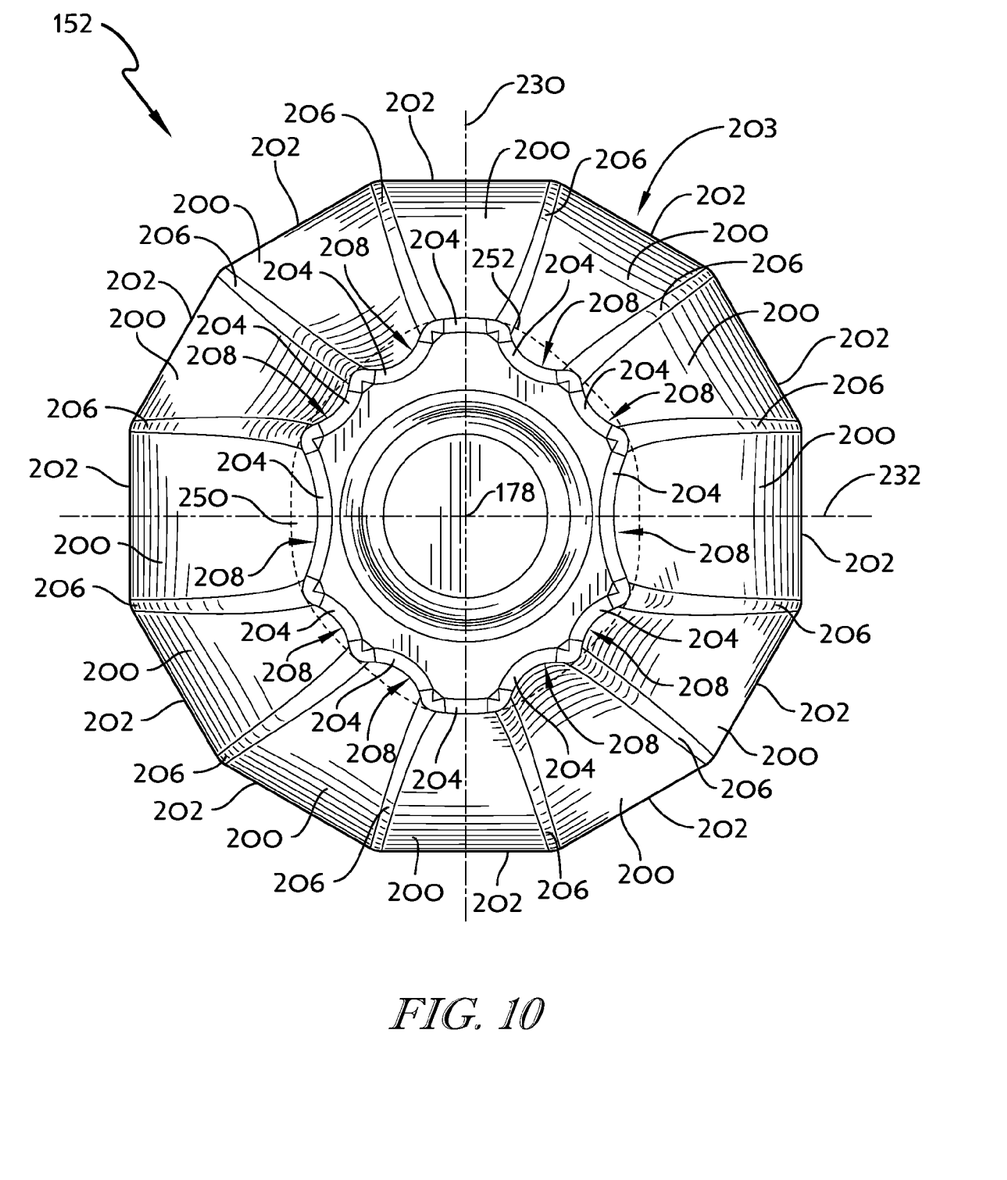
FIG. 10 is a bottom elevational view of the refill of FIG. 5.

Referring to FIGS. 7 and 10, each second wall portion 200 shares a side edge or vertex 206 with adjacent second wall portions 200, wherein each second wall portion 200 extends between adjacent vertices 206. The second wall portions 200 are concave such that they create flutes 208 between the vertices 206. One or more of the wall portions 200 may be convex or relatively planar to aid in manufacturing the refill 150. As best seen in FIG. 10, the flutes 208 create gaps between the vertices 206, thereby creating an airflow path, as discussed in detailed with respect to the embodiment of FIGS. 1-5. In illustrative embodiments, the flutes 208 may have a radius of curvature of between about 0.1 inch (2.54 mm) and about 0.4 inch (10.16 mm). As seen in FIG. 10, the radius of curvature of each of the flutes 208 may be different and each may range between about 0.1 inch (2.54 mm) and about 0.4 inch (10.16 mm). In an illustrative embodiment, the radius of curvature for each flute 108 is the same. In another illustrative embodiment, the radius of curvature of each flute 108 may be different or any number of the flutes 108 may have different radii of curvature.

As noted above, when a typical refill is inserted into and retained within a volatile material dispenser, the refill is generally held in a manner in which airflow around the refill and into the dispenser is restricted. In contrast, when the refill 150 is inserted into the dispenser 400, the flutes 208 allow air to flow past the refill 50 to cool the dispenser 400, aid in volatile material emission, and/or provide any other suitable benefits. In particular, air may flow up the flutes 208, around the bottom edges 190 of the first wall portions 184 and through the dispenser 400, as shown by arrow 210 in FIG. 12.

As best seen in FIGS. 7 and 10, the top portion 185 of the refill 50 is symmetrical. In particular, the top portion 185 of the refill 150 is symmetrical about a first plane 220 that bisects the refill 150, comprises the longitudinal axis 178, and extends through two opposing vertices 186. The plane 220 may be rotated about the longitudinal axis 178 to extend through any two opposing vertices 186 or positioned to bisect any two opposing first wall portions 184 and the refill 150 will be symmetrical about the plane 220. The top portion 185 of the body 154 of the refill 150 is therefore rotational symmetrical through 360 degrees about the longitudinal axis 178 (and the plane 220).

The top portion 185 of the refill 150 is depicted as having rotational symmetry of the order 24 or 24-fold rotational symmetry with respect to the longitudinal axis 178 or the first plane 220. In this manner, if the plane 220 is rotated 15 degrees, the refill 150 remains symmetrical about the plane 220. While the refill 150 is depicted and described as having rotational symmetry on the order of 24 about the plane 220, in illustrative embodiments, the refill 150 may have rotational symmetry about the plane 220 of between 4-fold and 36-fold. In such illustrative embodiment, the refill 150 would be symmetrical if the plane 220 were rotated between about 10 degrees and about 90 degrees. In other illustrative embodiments, the refill 150 may have rotational symmetry about the plane 220 between 8-fold and 24-fold. In these illustrative embodiments, the refill 150 would be symmetrical if the plane 220, 222 were rotated about the longitudinal axis 178 between about 15 degrees and about 45 degrees.

Referring to FIGS. 7 and 10, the bottom portion 203 of the body 154 of the refill 150 is not rotationally symmetrical. Instead, the top edges 202 of the second wall portions 200 that form transition points 204 with the bottom edges 190 of the first wall portions 184 form the same rotationally symmetrical pattern as the first wall portions 184, but the bottom edges 205 of the second wall portions 200 are not rotationally symmetrical. Rather, each of the vertices 206 defining the second wall portions 200 is angled differently to form differently sized second wall portions 200 in order to create a bottom portion 203 that is not rotationally symmetrical.

While the bottom portion 203 is not rotationally symmetrical, the bottom portion 203 is symmetrical. Specifically, as seen in FIG. 10, the bottom portion 203 is symmetrical about a second plane 230 that extends through the longitudinal axis 178 of the refill 150 and bisects two opposing second wall portions 200. The bottom portion 203 is also symmetrical about a third plane 232 that extends through the longitudinal axis 178 of the refill 150, is perpendicular to the third plane 230, and bisects two opposing second wall portions 200.

The rotational symmetry of the top portion 185 of the body 154 of the refill 150 and the symmetry of the bottom portion 203 of the body 154 allow the refill 150 to be inserted and retained within a diffusion device in a few different manners, thereby allowing for easy and proper installation of the refill 150.

Referring to FIG. 9, if arcs 240 are drawn to connect each of the vertices 186 of the first wall portions 184 forming the top portion 185 of the body 154 with adjacent vertices 186, a circle 242 is formed. Each arc 240 is depicted as forming a sector of about 30 degrees of the entire circle. In other illustrative embodiments, each arc 240 may form a sector of the circle 242 of between about 18 degrees and about 90 degrees. In other illustrative embodiments, each arc 240 may form a sector of the circle of between about 22 degrees and about 45 degrees. A profile of the top portion 185 of the body 154 of the refill 150 may be circle at the top edge 188, the bottom edge 190, or in any plane formed perpendicular to both of the planes 120, 122 along the wall portions 184. While the arcs 240 are shown as forming a circle 242, other shapes may be formed without departing from the scope of the present invention.

As seen in FIG. 10, if arcs 250 are drawn to connect each of the vertices 206 of the second wall portions 200 forming the bottom portion 205 of the body 154 with adjacent vertices 206, an oval 252 is formed. While an oval is depicted, a pentagon, an ellipse, a rectangle, or any other suitable shape may be utilized. In the illustrated embodiment, the shape formed by the vertices 206 of the second wall portions 200 is symmetrical about two planes. In another embodiment, the shape formed by the vertices 206 of the second wall portions 200 is symmetrical about a single plane. In other illustrative embodiments, the shape may be completely asymmetrical.

The volatile material disposed in the containers 54, 154 may be any type of volatile material adapted to be dispensed into an environment. For example, the containers 54, 154 may include a cleaner, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Additives may be included in the volatile material, such as, for example, fragrances and/or preservatives.

Any of the embodiments described herein may be modified to include any of the structures or methodologies disclosed in connection with other embodiments.

Further, although directional terminology, such as front, back, top, bottom, upper, lower, etc. may be used throughout the present specification, it should be understood that such terms are not limiting and are only utilized herein to convey the orientation of different elements with respect to one another.

All documents cited in the Detailed Description are, in relevant part, incorporated herein by reference; the citation of any document is not to be construed as an admission that it is prior art with respect to the present disclosure.

INDUSTRIAL APPLICABILITY

The present invention provides refills that may include one or more features that provide increased airflow around the refills. In particular, the refills may include one or more wall portions that are concave to provide flutes that provide a pathway for movement of air. Alternatively, or in addition, some of the refills of the present invention may be symmetrical or rotationally symmetrical to aid a user during insertion of the refills within a volatile material dispenser.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

We claim:
1. A volatile material dispenser, comprising:
a housing including a feature for retaining a refill; and
a refill retained within the housing and including:
a body adapted to hold a volatile material and including:
a first plurality of walls extending between a neck of the refill and a transition point, wherein each of the first plurality of walls curves outwardly and downwardly from the neck of the refill;
a second plurality of walls extending between the first plurality of walls and a bottom of the refill, wherein each of the second plurality of walls tapers inwardly from the transition point to the bottom of the refill;

wherein each transition point forms a ledge; and wherein a longitudinal axis of the body extends through a center of the body and the body is rotationally symmetrical about the longitudinal axis; and a wick disposed within the body and extending out of the refill, wherein the wick is adapted to transport the volatile material from the body out of the refill;

wherein the feature cooperates with the ledge to retain the refill within the housing and each of the second plurality of walls is configured to allow airflow along the body of the refill.

2. The dispenser of claim 1, wherein the refill has rotational symmetry about the longitudinal axis between 4-fold and 36-fold.

3. The dispenser of claim 2, wherein the refill has rotational symmetry about the longitudinal axis between 10-fold and 20-fold.

4. The dispenser of claim 1, wherein a first plane is coincident with the longitudinal axis and bisects the body of the refill and the body of the refill is rotationally symmetrical about the first plane.

5. The dispenser of claim 4, wherein a second plane is coincident with the longitudinal axis, perpendicular to the first plane, and bisects the body and the body is rotationally symmetrical about the second plane.

6. The dispenser of claim 4, wherein the refill has rotational symmetry about the second plane between 4-fold and 36-fold.

7. The dispenser of claim 6, wherein the refill has rotational symmetry about the second plane between 10-fold and 20-fold.

8. The dispenser of claim 1, wherein the body of the refill includes a plurality of walls including wall portions having concave surfaces for providing the airflow along the body.

9. A volatile material dispenser, comprising:

a housing including a feature for retaining a refill; and a refill retained within the housing and including:

a body adapted to hold a volatile material and including:

a plurality of walls each having first and second vertices shared with adjacent walls, an upper edge, and a lower edge adjacent a bottom wall of the body;

wherein each of the adjacent walls includes a first portion and a second, tapered portion extending from the first portion, wherein a first edge of each tapered portion adjacent a corresponding first portion is substantially straight and a second edge of the tapered portion adjacent the bottom wall of the body is concave to create flutes along the tapered portions;

wherein the first and second portions meet at the first edges to form a ledge; and a wick disposed within the body and extending out of the refill, wherein the wick is adapted to transport the volatile material from the body out of the refill;

wherein the feature cooperates with the ledge to retain the refill within the housing and each of the second plurality of walls is configured to allow airflow along the body of the refill.

10. The dispenser of claim 9, wherein a longitudinal axis of the body extends through a center of the body, each of the first portions of the plurality of walls is rotationally symmetrical about the longitudinal axis, and each of the second portions of the plurality of walls is not rotationally symmetrical about the longitudinal axis.

11. The dispenser of claim 9, wherein each of the walls of the refill includes flutes has a radius of curvature of between about 0.1 inch (2.54 mm) and about 0.4 inch (10.16 mm).

12. The dispenser of claim 9, wherein each of the first portions is joined to an adjacent first portion by first vertices and each of the second portions is joined to an adjacent second portion by second vertices and wherein arcs connecting the first vertices form a first shape and arcs connecting the second vertices form a second shape different than the first shape.

13. The dispenser of claim 12, wherein the first shape is a circle and the second shape is an oval.

14. A volatile material dispenser, comprising:

a housing including a feature for retaining a refill; and a refill retained within the housing and including:

a body adapted to hold a volatile material and including:

a first plurality of walls extending between a neck of the refill and a transition point, wherein each of the first plurality of walls curves outwardly and downwardly from the neck of the refill;

a second plurality of walls extending between the first plurality of walls and a bottom of the refill, wherein each of the second plurality of walls tapers inwardly from the transition point to the bottom of the refill;

wherein each transition point forms a ledge; and wherein a longitudinal axis of the body extends through a center of the body, the first plurality of walls is rotationally symmetrical about the longitudinal axis, and the second plurality of walls is not rotationally symmetrical about the longitudinal axis; and a wick disposed within the body and extending out of the refill, wherein the wick is adapted to transport the volatile material from the body out of the refill;

wherein the feature cooperates with the ledge to retain the refill within the housing and each of the second plurality of walls is configured to allow airflow along the body of the refill.

15. The dispenser of claim 14, wherein each of the second plurality of walls of the refill is curved inwardly between the side edges to form flutes.

16. The dispenser of claim 14, wherein each of the first plurality of walls of the refill has rotational symmetry about the longitudinal axis between 4-fold and 36-fold.

17. The dispenser of claim 16, wherein each of the first plurality of walls of the refill has rotational symmetry about the longitudinal axis between 10-fold and 20-fold.

* * * * *